United States Patent [19]

Li

[11] 4,408,087

[45] Oct. 4, 1983

[54] PURIFICATION OF BISPHENOL-A

[75] Inventor: Ming K. Li, Schenectady, N.Y.

[73] Assignee: General Electric Company, Schenectady, N.Y.

[21] Appl. No.: 88,768

[22] Filed: Oct. 29, 1979

[51] Int. Cl.$^3$ .................. C07C 29/92; C07C 29/78
[52] U.S. Cl. .................................................. 568/724
[58] Field of Search ........................................ 568/724

[56] References Cited

U.S. PATENT DOCUMENTS 2,791,616  5/1957  Luten, Jr. ............................ 568/724
3,326,986  6/1967  Dugan et al. ....................... 568/724

FOREIGN PATENT DOCUMENTS 1580676  7/1969  France ................................ 568/724
 946322  1/1964  United Kingdom ............... 568/724

Primary Examiner—J. E. Evans
Attorney, Agent, or Firm—William H. Pittman; James C. Davis, Jr.; James Magee, Jr.

[57] ABSTRACT

Pure bisphenol-A can be obtained by treating the adduct of the latter and phenol with water in two stages.

3 Claims, No Drawings

PURIFICATION OF BISPHENOL-A

This invention is concerned with the purification of 2,2-bis(4-hydroxyphenyl)propane (hereinafter identified as "bisphenol-A" or "BPA"). More particularly, the invention is directed to a method for recovering bisphenol-A in a purified state from a mixture of the latter and impurities derived from the acid-catalyzed condensation of phenol and acetone, which method comprises (1) intimately admixing a mixture of (a) an adduct of phenol and the above-identified dihydroxydiphenyl propane and (b) impurities associated with (a), with from 1 to 4 parts by weight, water per part by weight of adduct, (2) heating the mixture of the adduct and water at a temperature of from 85° to 110° C. to form a two-phase liquid aqueous-organic system, (3) separating the organic phase from the aqueous phase formed in (2) thereby to obtain a substantially high content of bisphenol-A in the organic phase, (4) adding to the organic phase an amount of water less than that used in step (1) wherein the water is at a temperature in excess of 85° C., and (5) cooling the mixture thereby to precipitate the 2,2-bis(4-hydroxyphenyl) propane in a highly purified state substantially free of impurities which originally were present with the adduct.

Bisphenol-A is commercially prepared by reacting phenol and acetone in the presence of an acidic material such as sulfuric acid, hydrochloric acid, cation exchange resins, etc. As a result of carrying out this reaction, the bisphenol-A produced is accompanied by undesirable impurities such as the 2-(4-hydroxyphenyl)-2-(2-hydroxyphenyl)propane (hereinafter identified as "o-p-isomer") having the formula

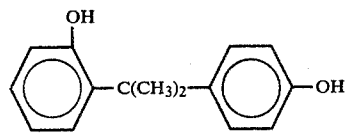

as well as other impurities including phenol itself used in making the bisphenol-A, a trishydroxyphenyl compound of the formula

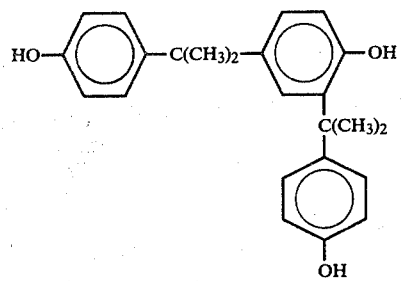

(hereinafter identified as "BPX-1", small amounts of other impurities such as the two compounds having the formulas

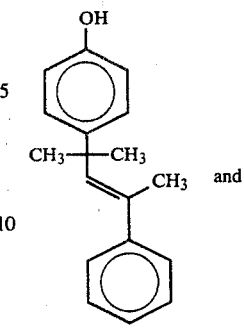

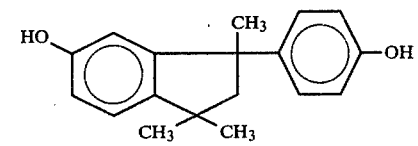

(hereinafter identified as "LD/CD", etc.

Since bisphenol-A is used in making polycarbonate resins by reaction of the latter with either phosgene or diphenyl carbonate, or for making epoxy resins, both resins being used extensively in commercial applications involving molding, casting, and sheet forming purposes, it is highly important that the monomeric bisphenol-A used to make such resins be as pure as possible in order to avoid adverse effects on the properties of the polymers thus obtained.

The preparation of the bisphenol-A by the reaction of phenol and acetone often leads to an adduct in which there is 1 mol of phenol per mol of the bisphenol-A together with any excess phenol which may have been used for reaction purposes. One method for working with this adduct to arrive at a purified bisphenol-A is described in Luten U.S. Pat. No. 2,791,616, issued May 7, 1957. According to this patent, the adduct obtained as a result of carrying out the initial reaction in the presence of the acidic condensation catalyst, uses an exceptionally excess of water within a well-defined temperature range which serves to liberate the phenol from the adduct with the result that most of the phenol is dissolved in the water while substantially all the bisphenol-A remains behind in the solid state. However, this process suffers from several disadvantages. Excessive amounts of water are usually required. Also, the water obtained containing the phenol, whether liberated from the adduct or the excess amount used in carrying out the initial condensation reaction, is in the form of a mixture which requires considerable processing and expenditure of energy in order to recover the phenol so that it can be used again for reaction with the acetone.

Another purification processing technique which has been employed after the adduct is broken is to subject the bisphenol-A to high temperature distillation to separate the latter from the impurities. In the process of using the high temperatures required (even under vacuum conditions) some of the BPA is lost through degradation and tar formation, thus contributing to a process which does not permit optimum yields of the bisphenol-A in a highly purified state.

Unexpectedly, I have discovered that I can treat the bisphenol-A adduct with water at elevated temperatures whereby the latter has been found capable of breaking the adduct thereby causing solution of the impurities in the water and the release of phenol either from the adduct or the residual phenol remaining from the reaction to make bisphenol-A. The resulting two-phase organic-aqueous reaction mixture is then separated and the organic phase containing the bisphenol-A with considerably less impurities and phenol residue than was present in the original bisphenol-A adduct is again treated with a smaller amount of water at elevated temperatures than was initially used (e.g., from 0.5 to 2 parts water per part bisphenol-A all on a weight basis), again, by cooling to precipitate solid bisphenol-A from the mixture, bisphenol-A is obtained in a highly purified state.

The initial treatment of the BPA-phenol adduct is carried out with an amount of water which, on a weight basis, is equal to 1 to 4 parts of the water per part of the adduct. By stirring this mixture and heating it to between 85° to 110° C., a two-phase system is obtained consisting of an organic phase and the aqueous phase. This two-phase system can be readily separated so that the organic phase is removed from the aqueous phase with the organic phase comprising mainly the adduct-free, purified bisphenol-A.

The second stage of treating the bisphenol-A, which is the predominant compound in the organic phase, requires even less water than was originally used for the first stage. Advantageously one can employ from about 0.5 to 2 parts of water per part of bisphenol-A comprising essentially the organic phase. The water added in the second stage must be at elevated temperatures, within the range of 85° to 110° C., to form again a two-phase organic-aqueous system. Instead of heating the mixture of the bisphenol-A and water in the second stage, it is often more efficient to introduce heated water within the above temperature range to the separated organic phase obtained from the first stage. Upon cooling the mixture to ambient temperature or higher (e.g., 40° to 75° C.) the highly purified crystalline bisphenol-A will precipitate and can easily be removed by filtration. If it is desired, one can then wash the crystals of bisphenol-A with methylene chloride as is more particularly described in my aforementioned U.S. Pat. No. 4,156,098. In this manner one can obtain BPA in a purity of well over 99% and approaching 100%.

My invention has major advantages over the process described in the above-mentioned Luten U.S. Pat. No. 2,791,616. According to Luten, water is added to the adduct mixture and heated at a temperature which maximizes at about 80° C. Thereafter, according to Luten, the mixture of the water and the adduct with the impurities therein as well as any residual phenol (which may be present as the result of added phenol or as a result of breaking the adduct), is cooled to a point where the bisphenol-A settles out. A this point, all liquid material is removed by filtration. In contrast to this, by employing a two-stage water treatment as described in my invention, one is able to use considerably less total water than is used ly Luten in carrying out his invention. This is clearly brought out in the Example 1 of the Luten patent where water is added to the adduct with its impurities in an amount equal to 25 times the weight of the phenol content of the adduct, and the resulting aqueous mixture is brought to a temperature of about 45° C., after which the bisphenol-A is precipitated from the aqueous phase.

In contrast to the above, my invention by operating at a temperature of from 85°–110° C., enables the adduct to be broken more readily so that the phenol thus liberated can be removed more efficiently and more rapidly by passage of the phenol into the aqueous phase. Even in the second stage treatment with water, it is again important that temperatures between 85°–110° C. are maintained in order to insure that essentially all of the phenol which may still be present in the bisphenol-A (as well as any residual impurities) is dissolved in the water. Even when this mixture as a two-phase system is cooled down to effect crystallization of the bisphenol-A, it will be found unexpectedly that the removed phenol and impurities will not pass back to contaminate the crystallizing bisphenol-A.

The term "bisphenol-A-phenol adduct" as used herein is intended to mean either (1) the adduct which is obtained as a result of the reaction of the phenol and the acetone in the presence of an acidic condensation catalyst, as well as (2) a preformed adduct which is made from impure bisphenol-A which has been treated with a sufficient amount of phenol to form the adduct. The molar concentration of the adduct consists of 1 mol of the bisphenol-A and 1 mol of phenol, and, on a weight basis, represents approximately 70 percent of the bisphenol-A and 30 percent phenol.

In carrying out my invention, the adduct is mixed throughly with the water in the first stage and is stirred at the elevated temperature for a time sufficient to cause the formation of the two-phase system. Thereafter, the second stage is pursued with the use of a smaller amount of water being added to the bisphenol-A which is now substantially freed from the adduct form. The crystallized bisphenol-A removed after the second stage water treatment can be rinsed with methylene chloride at room temperature to yield even higher purity bisphenol-A.

In order that those skilled in the art can better understand the present invention may be practiced, the following example is given by the way of illustration and not by way of limitation. Unless otherwise indicated, all parts are by weight.

The bisphenol-A adduct used in the following examples can be prepared in various ways. One example of such preparation is as follows:

EXAMPLE 1

Crude bisphenol-A (obtained from the reaction of phenol and acetone in the presence of an acidic catalyst, such as $H_2SO_4$) is dissolved with stirring in a large excess of phenol at a temperature of about 95° C. The adduct which precipitates is removed from the mother liquor consisting mostly of phenol and impurities. This procedure allows for a close simulation of the adduct that would be obtained in a bisphenol-A manufacturing plant.

EXAMPLE 2

About 140 grams of the above-identified bisphenol-A-phenol adduct with the impurities therein and 560 grams water (which represents about a 4 to 1 weight ratio of water to adduct) were heated with stirring to a temperature of about 96° C. until two liquid phases were observed to form. The agitation of the mixture was stopped to allow for phase separation. Five Hundred and twenty grams of an aqueous phase was removed. By cooling this aqueous phase to room temperature, a solid material precipitated which amounted to 10 grams of bisphenol-A. To the hot organic phase was added 360 grams of hot water at a temperature of about 80°–85° C. (so that the overall temperature was about 89° C.) and the mixture stirred and then allowed to cool to 65° C. to form a solid-liquid slurry. This slurry was subjected to a centrifuging action to yield 59 grams of solid bisphenol-A which was washed with 1.5 parts of methylene chloride pursuant to my U.S. Pat. No. 4,156,098 issued May 22, 1979 and assigned to the same assignee as the present invention.

The following table shows the composition analysis and the color absorbance characteristics of the solids at the various stages described above, it being recognized that there were small weight losses occasioned by handling and transfer during the operations.

The absorbance measurements were conducted by forming a 10% solid solution of the bisphenol-A in methanol and passing the solution through a 0.5 $\mu$m-pore size filter paper and then into a 10-cm quartz cell. The absorbance of this filtered solution was then determined in a spectrophotometer at 350 nm.

TABLE I

| [a]Ingredients % | Adduct | After Two $H_2O$ Separations | After $CH_2Cl_2$ Wash |
|---|---|---|---|
| Bisphenol-A | 67.38 | 99.16 | 99.66 |
| Phenol | 32.29 | 0.84 | 0.34 |
| [b]Impurities | 0.34 | Trace | Trace |
| Weight | 140 g. | 59 g. | — |
| Absorbance of adduct or BPA | 0.138 | 0.093 | — |

[a]The crystalline bisphenol-A was analyzed by liquid chromotography for weights percent of the bisphenol-A and their impurities.
[b]Impurities include o,p-isomer, LD/CD and BPX-1

It will be noted from the above Example 2 that despite using less water than is used in the working example of the aforementioned Luten patent, the purity of this bisphenol-A was extremely high and substantially unchanged from that resulting even when washed with $CH_2Cl_2$.

It will of course be understood by those skilled in the art that in addition to the conditions and proportion of ingredients employed in the foregoing examples, other conditions of admixture, filtering, washing, and separating, ratios of the adduct to water, and temperatures may be employed without departing from the scope of the intended invention more particularly described above.

What I claim as new and desire to secure by Letters Patent in the United States :

1. The method of recovering 2,2-bis(4-hydroxyphenyl)propane in a purified state from a mixture of the latter and impurities derived from the acid condensation of phenol and acetone which comprises:
    (1) combining a mixture of (a) an adduct of phenol and said 2,2-bis(4-hydroxyphenyl)propane and (b) impurities associated with (a), with from 1 to 4 parts, by weight, water per weight part of adduct,
    (2) heating the mixture of the adduct and water at a temperature from 85° to 110° C., to break said adduct and form a two-phase liquid aqueous-organic system,
    (3) separating the organic phase containing said 2,2-bis(4-hydroxyphenyl)propane from the aqueous phase formed in (2) while the two phases are at an elevated temperature,
    (4) adding the organic phase an amount of water less than that used in step (1), wherein the water and organic phase mixture is at a temperature of at least 85° C., and
    (5) cooling the mixture to precipitate said 2,2-bis(4-hydroxyphenyl)propane in a highly purified state.

2. The method as in claim 1 wherein the precipitated 2,2-bis(4-hydroxyphenyl)propane is treated with methylene chloride.

3. The method as in claim 1 wherein the water used in step (4) is equal, by weight, to 0.5 to 2 parts per part 2,2-bis(4-hydroxyphenyl)propane.

* * * * *